US011440988B2

(12) United States Patent
Ekin et al.

(10) Patent No.: US 11,440,988 B2
(45) Date of Patent: *Sep. 13, 2022

(54) POLYURETDIONE-CONTAINING RESIN BLEND COMPOSITIONS

(71) Applicants: Covestro LLC, Pittsburgh, PA (US); Covestro Deutschland AG, Leverkusen (DE)

(72) Inventors: Alan Ekin, Coraopolis, PA (US); Florian Johannes Stempfle, Cologne (DE); Alan D. Bushmire, Canonsburg, PA (US)

(73) Assignees: Covestro LLC, Pittsburgh, PA (US); Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/933,511

(22) Filed: Mar. 23, 2018

(65) Prior Publication Data

US 2019/0292295 A1   Sep. 26, 2019

(51) Int. Cl.
| | |
|---|---|
| C08G 18/02 | (2006.01) |
| C08G 18/79 | (2006.01) |
| C08K 5/31 | (2006.01) |
| C08K 5/3467 | (2006.01) |
| C08G 18/20 | (2006.01) |
| C09D 175/04 | (2006.01) |
| C08G 18/18 | (2006.01) |
| C08G 18/42 | (2006.01) |
| C08G 18/62 | (2006.01) |
| C08G 18/44 | (2006.01) |
| C09J 175/04 | (2006.01) |
| C08G 18/78 | (2006.01) |
| C08G 18/48 | (2006.01) |
| C07D 471/04 | (2006.01) |

(52) U.S. Cl.
CPC ....... *C08G 18/027* (2013.01); *C08G 18/1858* (2013.01); *C08G 18/2027* (2013.01); *C08G 18/2036* (2013.01); *C08G 18/2072* (2013.01); *C08G 18/42* (2013.01); *C08G 18/4277* (2013.01); *C08G 18/44* (2013.01); *C08G 18/48* (2013.01); *C08G 18/6229* (2013.01); *C08G 18/7837* (2013.01); *C08G 18/797* (2013.01); *C08G 18/798* (2013.01); *C08K 5/31* (2013.01); *C08K 5/3467* (2013.01); *C09D 175/04* (2013.01); *C09J 175/04* (2013.01); *C07D 471/04* (2013.01); *C08G 2190/00* (2013.01)

(58) Field of Classification Search
CPC .............. C08G 18/027; C08G 18/2072; C08G 18/798; C08G 18/4277; C08G 18/7837; C08G 18/797; C08G 18/44; C08G 18/6229; C08G 18/2036; C08G 18/2027; C08G 18/1858; C08G 18/42; C08G 18/48; C08G 2190/00; C08K 5/3467; C08K 5/31; C07D 471/04; C09D 175/04; C09J 175/04

See application file for complete search history.

(56) References Cited

U.S. PATENT DOCUMENTS

| | | |
|---|---|---|
| 3,169,949 A | 2/1965 | Büning |
| 5,814,689 A | 9/1998 | Goldstein et al. |
| 5,861,193 A | 1/1999 | Goldstein et al. |
| 5,916,629 A | 6/1999 | Wenning et al. |
| 8,791,223 B2 | 7/2014 | Zalich et al. |
| 9,080,074 B2 | 7/2015 | Shaffer et al. |
| 9,102,785 B2 | 8/2015 | Martz et al. |
| 2006/0052527 A1 | 3/2006 | Weikard et al. |
| 2006/0247341 A1 | 11/2006 | Hsieh et al. |
| 2008/0194787 A1* | 8/2008 | Weiss ................. C08G 18/0895 528/67 |
| 2009/0264587 A1 | 10/2009 | Blum et al. |
| 2012/0225982 A1* | 9/2012 | Ravichandran ...... C08K 5/0091 524/196 |
| 2014/0275345 A1* | 9/2014 | Williams ................. C09D 4/00 523/445 |
| 2015/0232609 A1 | 8/2015 | Spryou et al. |
| 2016/0017179 A1 | 1/2016 | Spyrou et al. |

FOREIGN PATENT DOCUMENTS

DE   102008040967 A1   2/2010

* cited by examiner

*Primary Examiner* — Rabon A Sergent
(74) *Attorney, Agent, or Firm* — John E. Mrozinski, Jr.

(57) ABSTRACT

The present invention provides a reaction mixture comprising a blend of a first isocyanate-based uretdione-containing resin and a second isocyanate-based uretdione-containing resin, a neutralized polyol and a tertiary amine catalyst, and optionally, an additive package selected from the group consisting of flow control additives, pigments (colorants), wetting agents, and solvents, wherein the first isocyanate and the second isocyanate are different. The first isocyanate-based uretdione-containing resin and the second isocyanate-based uretdione-containing resin may be cold blended or hot blended. Coatings, adhesives, castings, composites, and sealants made from hot blended formulations exhibit superior performance over those made from cold blended formulations.

9 Claims, No Drawings

POLYURETDIONE-CONTAINING RESIN BLEND COMPOSITIONS

FIELD OF THE INVENTION

The present invention relates, in general to polymers, and more specifically, to polymers made with blended isocyanate-based uretdione-containing resins, neutralized polyols, and tertiary amine catalysts. The resulting allophanate polymers may be used to make coatings, adhesives, castings, composites, and sealants.

BACKGROUND OF THE INVENTION

Polyurethane-forming compositions are widely used in a variety of commercial, industrial and household applications, such as in automotive clear-coat and seat cushion applications. Polyurethane systems that employ isocyanates which are pre-reacted with monofunctional reagents to form relatively thermally labile compounds are called blocked isocyanates. Uretdiones are a type of blocked isocyanate. Uretdiones are typically prepared by dimerizing an isocyanate to form uretdione(s) with unreacted isocyanate endgroups which can then be extended with a polyol to form a polymeric material containing two or more uretdione groups in the polymer chain. In some literature, uretdiones are referred to as "1,3-diaza-2,4-cyclobutanones", "1,3-diazatidin-2,4-diones", "2,4-dioxo-1,3-diazetidines", "urethdiones" or "uretidiones". Typically, the polymer has few, if any, free isocyanate groups, which is achieved by controlling the stoichiometry of the polyisocyanate, polyol and by the use of a blocking agent.

The reaction of uretdiones with polyols to form polyurethane coatings is well known in the art, especially in polyurethane powder coatings. However, the creation of allophanates from isocyanate-based uretdiones containing resins and polyols at ambient or low temperatures in the presence of tertiary amine catalysts has not been well-studied in the literature. To the best of the present inventors' knowledge, no one has developed a cross-linking approach using neutralized polyols to promote successful conversion of uretdione to allophanate at ambient or low temperatures in the presence of tertiary amine catalysts.

SUMMARY OF THE INVENTION

Accordingly, the present invention reduces or eliminates problems inherent in the art by providing a reaction mixture comprising a blend of a first isocyanate-based uretdione-containing resin and a second isocyanate-based uretdione-containing resin; a neutralized polyol and a tertiary amine catalyst; and optionally, an additive package selected from the group consisting of flow control additives, pigments (colorants), wetting agents, and solvents, wherein the first isocyanate and the second isocyanate are different. The first isocyanate-based uretdione-containing resin and the second isocyanate-based uretdione-containing resin may be cold blended or hot blended.

Uretdione-containing resins can be crosslinked with polyols to form allophanate groups in the presence of tertiary amine catalysts. Uretdiones can be made by catalytic dimerization of isocyanates. After dimerization, the remaining isocyanates can be reacted with polyols (diols, monools) to increase functionality and/or molecular weight. Different isocyanate-based uretdione-containing resins can be made separately using polyols (diols, monools) in flasks, reactors, or vessels and later cold blended. The cold blended uretdione-containing resins can then be formulated with neutralized polyols and tertiary amine catalysts to provide optimum performance. In addition, hot blended uretdione-containing resins can be made by reacting two or more of different kinds of uretdione-containing resins in the same flasks, reactors, or vessels, and then reacting the remaining isocyanates with polyols (diols, monools). The hot blended uretdione-containing resins can be formulated with neutralized polyols and tertiary amine catalysts to provide optimum performance. The present inventors have unexpectedly discovered that coatings, adhesives, castings, composites, and sealants made from formulations that were made from hot blended uretdione containing resins exhibit superior performance over those formulations that were made from cold blended uretdione containing resins.

These and other advantages and benefits of the present invention will be apparent from the Detailed Description of the Invention herein below.

DETAILED DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about."

Any numerical range recited in this specification is intended to include all sub-ranges of the same numerical precision subsumed within the recited range. For example, a range of "1.0 to 10.0" is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited in this specification is intended to include all lower numerical limitations subsumed therein and any minimum numerical limitation recited in this specification is intended to include all higher numerical limitations subsumed therein. Accordingly, Applicants reserve the right to amend this specification, including the claims, to expressly recite any sub-range subsumed within the ranges expressly recited herein. All such ranges are intended to be inherently described in this specification such that amending to expressly recite any such sub-ranges would comply with the requirements of 35 U.S.C. § 112(a), and 35 U.S.C. § 132(a).

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

Reference throughout this specification to "various non-limiting embodiments," "certain embodiments," or the like, means that a particular feature or characteristic may be included in an embodiment. Thus, use of the phrase "in various non-limiting embodiments," "in certain embodiments," or the like, in this specification does not necessarily refer to a common embodiment, and may refer to different embodiments. Further, the particular features or characteristics may be combined in any suitable manner in one or more embodiments. Thus, the particular features or characteristics illustrated or described in connection with various or certain embodiments may be combined, in whole or in part, with the features or characteristics of one or more other embodiments without limitation. Such modifications and variations are intended to be included within the scope of the present specification.

The grammatical articles "a", "an", and "the", as used herein, are intended to include "at least one" or "one or more", unless otherwise indicated, even if "at least one" or "one or more" is expressly used in certain instances. Thus, these articles are used in this specification to refer to one or more than one (i.e., to "at least one") of the grammatical objects of the article. By way of example, and without limitation, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

In various embodiments, the present invention provides a reaction mixture comprising a blend of a first isocyanate-based uretdione-containing resin and a second isocyanate-based uretdione-containing resin; a neutralized polyol and a tertiary amine catalyst; and optionally, an additive package selected from the group consisting of flow control additives, pigments (colorants), wetting agents, and solvents, wherein the first isocyanate and the second isocyanate are different. In various embodiments, the first isocyanate-based uretdione-containing resin and the second isocyanate-based uretdione-containing resin may be cold blended or hot blended. Coatings, adhesives, castings, composites, and sealants made from hot blended formulations exhibit superior performance over those made from cold blended formulations.

In various non-limiting embodiments, the present invention further provides a method of making an allophanate polymer comprising blending a first isocyanate-based uretdione-containing resin and a second isocyanate-based uretdione-containing resin to form a resin blend, reacting the resin blend with a neutralized polyol in the presence of a tertiary amine catalyst, optionally in the presence of an additive package selected from the group consisting of flow control additives, pigments (colorants), wetting agents, and solvents, wherein the first isocyanate and the second isocyanate are different. The polyol may be neutralized by reaction with an acid scavenger at a temperature ranging from room temperature (21° C.-24° C.) to 12° C. Thus, the present invention provides a method for producing an allophanate polymer by the following route:

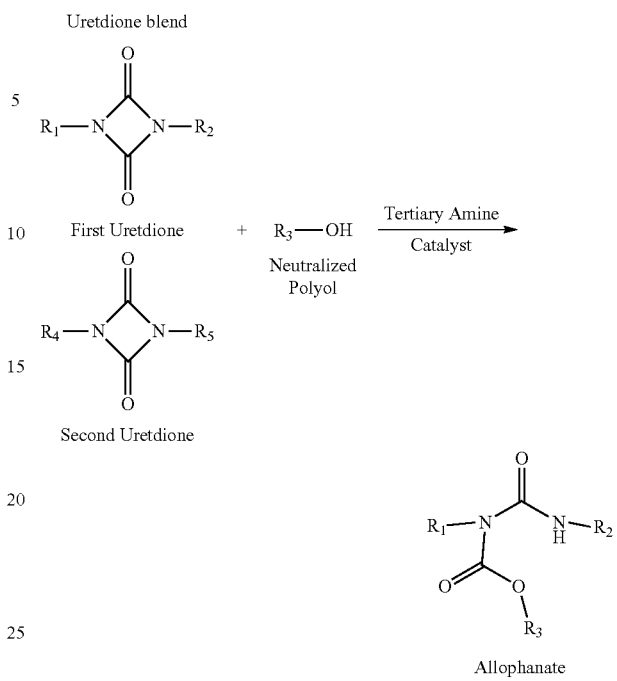

In the case of cold blending, $R_1$ and $R_2$ are the same but different than $R_3$ and $R_4$. Similarly, $R_3$ and $R_4$ are the same but different than $R_1$ and $R_2$. In case of hot blending, $R_1$, $R_2$, $R_3$, and $R_4$ may be independently the same or different. The scheme shows the reaction with uretdione from $R_1$ and $R_2$ forming an allophanate group. The second uretdione from $R_4$ and $R_5$ does form allophanate as well. The inventive allophanate polymer system is particularly applicable in coatings, adhesives, castings, composites, and sealants.

As used herein, the term "polymer" encompasses prepolymers, oligomers and both homopolymers and copolymers; the prefix "poly" in this context referring to two or more. As used herein, the term "molecular weight", when used in reference to a polymer, refers to the number average molecular weight, unless otherwise specified.

As used herein, the term "polyol" refers to compounds comprising at least two free hydroxy groups. Polyols include polymers comprising pendant and terminal hydroxy groups.

As used herein, the term "coating composition" refers to a mixture of chemical components that will cure and form a coating when applied to a substrate.

The terms "adhesive" or "adhesive compound", refer to any substance that can adhere or bond two items together. Implicit in the definition of an "adhesive composition" or "adhesive formulation" is the concept that the composition or formulation is a combination or mixture of more than one species, component or compound, which can include adhesive monomers, oligomers, and polymers along with other materials.

A "sealant composition" refers to a composition which may be applied to one or more surfaces to form a protective barrier, for example, to prevent ingress or egress of solid, liquid or gaseous material or alternatively to allow selective permeability through the barrier to gas and liquid. In particular, it may provide a seal between surfaces.

A "casting composition" refers to a mixture of liquid chemical components which is usually poured into a mold containing a hollow cavity of the desired shape, and then allowed to solidify.

A "composite" refers to a material made from two or more polymers, optionally containing other kinds of materials. A composite has different properties from those of the individual polymers/materials which make it up.

"Cured," "cured composition" or "cured compound" refers to components and mixtures obtained from reactive curable original compound(s) or mixture(s) thereof which have undergone a chemical and/or physical changes such that the original compound(s) or mixture(s) is(are) transformed into a solid, substantially non-flowing material. A typical curing process may involve crosslinking.

The term "curable" means that an original compound(s) or composition material(s) can be transformed into a solid, substantially non-flowing material by means of chemical reaction, crosslinking, radiation crosslinking, or the like. Thus, compositions of the invention are curable, but unless otherwise specified, the original compound(s) or composition material(s) is(are) not cured.

As used in the context of the present invention, "hot blended" or "hot blending" means taking a first isocyanate-based uretdione-containing resin and a second isocyanate-based uretdione-containing resin and mixing them together in a flask, reactor, or other vessel, with heating while reacting with the appropriate polyol(s) to obtain a uretdione blend with specific functionality and molecular weight. The resulting hot blends may be liquid when cooled to room temperature after completion of the reaction.

As used herein, "cold blended" or "cold blending" means the first isocyanate-based uretdione-containing resin and the second isocyanate-based uretdione-containing resin are made in separate flasks, reactors, or other vessels, with the appropriate polyols to achieve a specific functionality and molecular weight. After the completion of the reactions of uretdione-containing resins with polyols, the resins are cooled down to room temperature for cold blending. The first isocyanate-based uretdione-containing resin and the second isocyanate-based uretdione-containing resin are then mixed together at specified ratios. The resulting cold blends may be liquid.

After cold and hot blends are made, coatings, adhesives, castings, composites, and sealants formulations are made by addition of the appropriate polyol and catalyst to the blend.

The components useful in the present invention comprise a polyisocyanate. As used herein, the term "polyisocyanate" refers to compounds comprising at least two unreacted isocyanate groups, such as three or more unreacted isocyanate groups. The polyisocyanate may comprise diisocyanates such as linear aliphatic polyisocyanates, aromatic polyisocyanates, cycloaliphatic polyisocyanates and aralkyl polyisocyanates.

Particularly preferred in the present invention are those blocked isocyanates known as uretdiones. The uretdiones useful in the invention may be obtained by catalytic dimerization of polyisocyanates by methods which are known to those skilled in the art. Examples of dimerization catalysts include, but are not limited to, trialkylphosphines, aminophosphines and aminopyradines such as dimethylaminopyridines, and tris(dimethylamino)phosphine, as well as any other dimerization catalyst. The result of the dimerization reaction depends, in a manner known to the skilled person, on the catalyst used, on the process conditions and on the polyisocyanates employed. In particular, it is possible for products to be formed which contain on average more than one uretdione group per molecule, the number of uretdione groups being subject to a distribution. The (poly)uretdiones may optionally contain isocyanurate, biuret, allophanate, and iminooxadiazine dione groups in addition to the uretdione groups.

The uretdiones are NCO-functional compounds and may be subjected to a further reaction, for example, blocking of the free NCO groups or further reaction of NCO groups with NCO-reactive compounds having a functionality of two or more to extend the uretdiones to form polyuretdione pre-polymers. This gives compounds containing uretdione groups and of higher molecular weight, which, depending on the chosen proportions, may also contain NCO groups, be free of NCO groups or may contain isocyanate groups that are blocked.

Suitable blocking agents include, but are not limited to, alcohols, lactams, oximes, malonates, alkyl acetoacetates, triazoles, phenols, imidazoles, pyrazoles and amines, such as butanone oxime, diisopropylamine, 1,2,4-triazole, dimethyl-1,2,4-triazole, imidazole, diethyl malonate, ethyl acetoacetate, acetone oxime, 3,5-dimethylpyrazole, caprolactam, N-tert-butylbenzylamine and cyclopentanone including mixtures of these blocking agents.

Examples of NCO-reactive compounds with a functionality of two or more include polyols. In some embodiments, the NCO-reactive compounds are used in amounts sufficient to react with all free NCO groups in the uretdione. By "free NCO groups" it is meant all NCO groups not present as part of the uretdione, isocyanurate, biuret, allophanate and iminooxadiazine dione groups.

The resulting polyuretdione contains at least 2, such as from 2 to 10 uretdione groups. More preferably, the polyuretdione contains from 5% to 45% uretdione, 10% to 55% urethane, and less than 2% isocyanate groups. The percentages are by weight based on total weight of resin containing uretdione, urethane, and isocyanate.

Suitable polyisocyanates for producing the uretdiones useful in embodiments of the invention include, organic diisocyanates represented by the formula

wherein R represents an organic group obtained by removing the isocyanate groups from an organic diisocyanate having (cyclo)aliphatically bound isocyanate groups and a molecular weight of 112 to 1000, preferably 140 to 400. Preferred diisocyanates for the invention are those represented by the formula wherein R represents a divalent aliphatic hydrocarbon group having from 4 to 18 carbon atoms, a divalent cycloaliphatic hydrocarbon group having from 5 to 15 carbon atoms, or a divalent araliphatic hydrocarbon group having from 7 to 15 carbon atoms.

Examples of the organic diisocyanates which are suitable for the present invention include 1,4-tetramethylene diisocyanate, 1,6-hexamethylene diisocyanate (HDI), 2,2,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyanatocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydrotoluene diisocyanate, toluene diisocyanate (TDI), diphenylmethane diisocyanate (MDI), pentane diisocyanate (PDI)—bio-based, and, isomers of any of these; or combinations of any of these. Mixtures of diisocyanates may also be used.

Particularly preferred diisocyanates are 1,6-hexamethylene diisocyanate (HDI) and isophorone diisocyanate (IPDI).

In some embodiments, the uretdiones may comprise from 35% to 85% resin solids in the composition of present invention, excluding solvents, additives or pigments. In other embodiments, from 50% to 85% and in still other embodiments, 60% to 85%. The uretdiones may comprise any resin solids amount ranging between any combinations of these values, inclusive of the recited values.

In various embodiments of the present invention, the reaction mixture containing the polyuretdione and the neutralized polyol in the presence of a tertiary amine catalyst may be heated to a temperature of 140° C., in other embodiments to a temperature of from 20° C. to 140° C.

The polyols useful in the present invention may be either low molecular weight (62-399 Da, as determined by gel permeation chromatography) or high molecular weight (400 to 10,000 Da, as determined by gel permeation chromatography) materials and in various embodiments will have average hydroxyl values as determined by ASTM E222-10, Method B, of between 1000 and 10, and preferably between 500 and 50.

The polyols in the present invention include low molecular weight diols, triols and higher alcohols and polymeric polyols such as polyester polyols, polyether polyols, polycarbonate polyols, polyurethane polyols and hydroxy-containing (meth)acrylic polymers.

The low molecular weight diols, triols and higher alcohols useful in the instant invention are known to those skilled in the art. In many embodiments, they are monomeric and have hydroxy values of 200 and above, usually within the range of 1500 to 200. Such materials include aliphatic polyols, particularly alkylene polyols containing from 2 to 18 carbon atoms. Examples include ethylene glycol, 1,4-butanediol, 1,6-hexanediol; cycloaliphatic polyols such as cyclohexane dimethanol. Examples of triols and higher alcohols include trimethylol propane and pentaerythritol. Also useful are polyols containing ether linkages such as diethylene glycol and triethylene glycol.

In various embodiments, the suitable polyols are polymeric polyols having hydroxyl values less than 200, such as 10 to 180. Examples of polymeric polyols include polyalkylene ether polyols, polyester polyols including hydroxyl-containing polycaprolactones, hydroxy-containing (meth)acrylic polymers, polycarbonate polyols and polyurethane polymers.

Examples of polyether polyols include poly(oxytetramethylene) glycols, poly(oxyethylene) glycols, and the reaction product of ethylene glycol with a mixture of propylene oxide and ethylene oxide.

Also useful are polyether polyols formed from the oxyalkylation of various polyols, for example, glycols such as ethylene glycol, 1,4-butane glycol, 1,6-hexanediol, and the like, or higher polyols, such as trimethylol propane, pentaerythritol and the like. One commonly utilized oxyalkylation method is by reacting a polyol with an alkylene oxide, for example, ethylene oxide in the presence of an acidic or basic catalyst.

Polyester polyols can also be used as a polymeric polyol component in the certain embodiments of the invention. The polyester polyols can be prepared by the polyesterification of organic polycarboxylic acids or anhydrides thereof with organic polyols. Preferably, the polycarboxylic acids and polyols are aliphatic or aromatic dibasic acids and diols.

The diols which may be employed in making the polyester include alkylene glycols, such as ethylene glycol and butylene glycol, neopentyl glycol and other glycols such as cyclohexane dimethanol, caprolactone diol (for example, the reaction product of caprolactone and ethylene glycol), polyether glycols, for example, poly(oxytetramethylene) glycol and the like. However, other diols of various types and, as indicated, polyols of higher functionality may also be utilized in various embodiments of the invention. Such higher polyols can include, for example, trimethylol propane, trimethylol ethane, pentaerythritol, and the like, as well as higher molecular weight polyols such as those produced by oxyalkylating low molecular weight polyols. An example of such high molecular weight polyol is the reaction product of 20 moles of ethylene oxide per mole of trimethylol propane.

The acid component of the polyester consists primarily of monomeric carboxylic acids or anhydrides having 2 to 18 carbon atoms per molecule. Among the acids which are useful are phthalic acid, isophthalic acid, terephthalic acid, tetrahydrophthalic acid, hexahydrophthalic acid, adipic acid, azelaic acid, sebacic acid, maleic acid, glutaric acid, chlorendic acid, tetrachlorophthalic acid and other dicarboxylic acids of varying types. Also, there may be employed higher polycarboxylic acids such as trimellitic acid and tricarballylic acid (where acids are referred to above, it is understood that the anhydrides of those acids which form anhydrides can be used in place of the acid). Also, lower alkyl esters of acids such as dimethyl glutamate can be used.

Besides polyester polyols formed from polybasic acids and polyols, polycaprolactone-type polyesters can also be employed. These products are formed from the reaction of a cyclic lactone such as ε-caprolactone with a polyol with primary hydroxyls such as those mentioned above. Such products are described in U.S. Pat. No. 3,169,949.

In addition to the polyether and polyester polyols, hydroxy-containing (meth)acrylic polymers or (meth)acrylic polyols can be used as the polyol component.

Among the (meth)acrylic polymers are polymers of 2 to 20 percent by weight primary hydroxy-containing vinyl monomers such as hydroxyalkyl acrylate and methacrylate having 2 to 6 carbon atoms in the alkyl group and 80 to 98 percent by weight of other ethylenically unsaturated copolymerizable materials such as alkyl(meth)acrylates; the percentages by weight being based on the total weight of the monomeric charge.

Examples of suitable hydroxy alkyl(meth)acrylates are hydroxy ethyl and hydroxy butyl(meth)acrylate. Examples of suitable alkyl acrylates and (meth)acrylates are lauryl methacrylate, 2-ethylhexyl methacrylate and n-butyl acrylate.

In addition to the acrylates and methacrylates, other copolymerizable monomers which can be copolymerized with the hydroxyalkyl (meth)acrylates include ethylenically unsaturated materials such as monoolefinic and diolefinic hydrocarbons, halogenated monoolefinic and diolefinic hydrocarbons, unsaturated esters of organic and inorganic acids, amides and esters of unsaturated acids, nitriles and unsaturated acids and the like. Examples of such monomers include styrene, 1,3-butadiene, acrylamide, acrylonitrile, α-methyl styrene, α-methyl chlorostyrene, vinyl butyrate, vinyl acetate, alkyl chloride, divinyl benzene, diallyl itaconate, triallyl cyanurate and mixtures thereof. Preferably, these other ethylenically unsaturated materials are used in admixture with the above-mentioned acrylates and methacrylates.

In certain embodiments of the invention, the polyol may be a polyurethane polyol. These polyols can be prepared by reacting any of the above-mentioned polyols with a minor amount of polyisocyanate (OH/NCO equivalent ratio greater than 1:1) so that free primary hydroxyl groups are present in the product. In addition to the high molecular weight polyols mentioned above, mixtures of both high molecular weight and low molecular weight polyols such as those mentioned above may be used.

Suitable hydroxy-functional polycarbonate polyols may be those prepared by reacting monomeric diols (such as 1,4-butanediol, 1,6-hexanediol, di-, tri- or tetraethylene glycol, di-, tri- or tetrapropylene glycol, 3-methyl-1,5-pentanediol, 4,4'-dimethylolcyclohexane and mixtures thereof) with diaryl carbonates (such as diphenyl carbonate, dialkyl carbonates (such as dimethyl carbonate and diethyl carbonate), alkylene carbonates (such as ethylene carbonate or propylene carbonate), or phosgene. Optionally, a minor amount of higher functional, monomeric polyols, such as trimethylolpropane, glycerol or pentaerythritol, may be used.

In various embodiments of the invention, the polyol is neutralized, for example by the addition of an acid scavenger. Acid scavengers should be covalently bonded to the acidic groups within the polyol. In various embodiments, the acid scavengers may be selected from carbodiimides, anhydrides, epoxies, trialkylorthoformates, amine compounds, and oxazolines. The present inventors believe, without wishing to be bound to any specific theory, that these acid scavengers covalently bind to carboxylic and acrylic acid groups within the polyols. Such compounds are commercially available from a variety of suppliers such as for example, the monomeric carbodiimides sold under the STABAXOL trade name from Rhein Chemie, and Bis(2,6-diisopropylphenyl) carbodiimide sold as EUSTAB HS-700 by Eutec Chemical Co., Ltd. In various embodiments, the neutralization is conducted at any temperature ranging from room temperature (21° C.-24° C.) to 120° C., in other embodiments from room temperature (21° C.-24° C.) to 80° C. and in certain embodiments at room to temperature (21° C.-24° C.).

In various embodiments of the present invention, the first and second isocyanate-based uretdione-containing resins may be blended (either hot blended or cold blended) at various ratios ranging from 92:8 to 24:76; in some embodiments the ratio may be 83:17 to 24:76; in yet other embodiments the ratio may be 74:26 and in still other embodiments the ratio may be 24:76 depending upon the identities of the first and second isocyanates.

Examples of suitable solvents include, but are not limited to aliphatic and aromatic hydrocarbons such as toluene, xylene, isooctane, acetone, butanone, methyl ethyl ketone, methyl amyl ketone, methyl isobutyl ketone, ethyl acetate, butyl acetate, pentyl acetate, tetrahydrofuran, ethyl ethoxypropionate, N-methyl-pyrrolidone, dimethylacetamide and dimethylformamide solvent naphtha, SOLVESSO 100 or HYDROSOL (ARAL), ethers, or mixtures thereof.

The compositions of the present invention may further include any of a variety of additives such as defoamers, devolatilizers, surfactants, thickeners, flow control additives, colorants (including pigments and dyes) or surface additives.

The composition of the invention may be contacted with a substrate by any methods known to those skilled in the art, including but not limited to, spraying, dipping, flow coating, rolling, brushing, pouring, and the like. In some embodiments, the inventive compositions may be applied in the form of paints or lacquers onto any compatible substrate, such as, for example, metals, plastics, ceramics, glass, and natural materials. In certain embodiments, the inventive composition is applied as a single layer. In other embodiments, the composition of the present invention may be applied as multiple layers as needed.

EXAMPLES

The non-limiting and non-exhaustive examples that follow are intended to further describe various non-limiting and non-exhaustive embodiments without restricting the scope of the embodiments described in this specification. All quantities given in "parts" and "percents" are understood to be by weight, unless otherwise indicated. Although the present invention is described in the instant Examples in the context of a coating, those skilled in the art will appreciate it can also be equally applicable to adhesives, castings, composites, and sealants. Further, although the present invention is exemplified with isophorone diisocyanate (IPDI) and 1,6-hexamethylene diisocyanate (HDI), any combination of different isocyanates will perform equally as well.

The following materials were used in preparing the compositions of the Examples:

| | |
|---|---|
| POLYOL A | an aromatic free, branched hydroxyl-bearing polyester polyol, commercially available from Covestro LLC as DESMOPHEN 775 XP; |
| ADDITIVE A | an active anti-hydrolysis agent for polyester polyurethanes, being used as an acid scavenger for acidic groups within the polyols, commercially available from Rhein Chemie as STABAXOL I; |
| ADDITIVE B | a surface additive on polyacrylate-basis for solvent-borne coating systems and printing inks, commercially available from BYK Chemie as BYK 358N; |
| CATALYST A | 1,8-diazabicyclo[5.4.0]undec-7-ene (DBU), tertiary amine catalyst, commercially available from Air Products as POLYCAT DBU; 10% CATALYST A solution was made in butyl acetate; |
| URETDIONE A | a 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 1,276 and a viscosity of 817 cPs in 50% butyl acetate; |
| URETDIONE B | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 824 and a viscosity of 8,250 cPs in 30% butyl acetate; |
| URETDIONE C | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 822 and a viscosity of 16,500 cPs in 30% butyl acetate; |
| URETDIONE D | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 820 and a viscosity of 15,300 cPs in 30% butyl acetate; |
| URETDIONE E | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 814 and a viscosity of 8,680 cPs in 30% butyl acetate; |

| | |
|---|---|
| URETDIONE F | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 812 and a viscosity of 22,500 cPs in 30% butyl acetate; |
| URETDIONE G | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 808 and a viscosity of 12,900 cPs in 30% butyl acetate; |
| URETDIONE H | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 809 and a viscosity of 9,220 cPs in 30% butyl acetate; |
| URETDIONE I | a 1,6-hexamethylene diisocyanate (HDI) and 1-isocyanato-3-isocyanatomethyl-3,5,5-trimethyl cyclohexane (isophorone diisocyanate or IPDI)-based uretdione prepolymer, proprietary product of Covestro LLC, having a uretdione equivalent weight of 808 and a viscosity of 18,800 cPs in 30% butyl acetate; |
| URETDIONE J | a 1,6-hexamethylene diisocyanate (HDI)-based uretdione prepolymer, proprietary product of Covestro LLC, having a uretdione equivalent weight of 871 and a viscosity of 10,800 cPs in 30% butyl acetate; |
| URETDIONE K | a 1,6-hexamethylene diisocyanate (HDI)-based uretdione prepolymer, proprietary product of Covestro LLC, having a uretdione equivalent weight of 624 and a viscosity of 31,200 cPs in 20% butyl acetate. |

Formulations A through AA in Table I were prepared following the same procedure. As an example, Formulation A was prepared as follows. POLYOL A had been reacted with ADDITIVE A prior to formulation. In a 100 mL plastic container 4.76 parts of the POLYOL A and ADDITIVE A reaction mixture, 0.19 parts ADDITIVE B, 0.98 parts CATALYST A (10% solution in butyl acetate (n-BA)), 1.70 parts n-butyl acetate, and 32.37 parts URETDIONE A were added. The resulting mixture was mixed using a FLACK-TEK speed mixer for one minute followed by application using a drawdown bar.

Zinc phosphate treated ACT B952, 3"×9" (7.62 cm×22.9) test panels were used. Thickness of coatings was 4 mils (100 μm) wet (2 mils (50 μm) dry). The resulting panels were used to test for MEK double rubs.

Films were cured at 100° C. for 30 minutes and allowed to stand for one day at room temperature before testing.

MEK double rubs were measured according to ASTM D4752-10(2015). Results reported are an average of three readings for each formulation.

In Table I, the number in parentheses following the URETDIONE indicates its functionality.

TABLE I

| | Ex. A | Ex. B | Ex. C | Ex. D | Ex. E | Ex. F | Ex. G | Ex. H | Ex. I | Ex. J | Ex. K | Ex. L |
|---|---|---|---|---|---|---|---|---|---|---|---|---|
| POLYOL A | 4.56 | 4.96 | 4.97 | 4.98 | 5.01 | 5.02 | 5.04 | 5.03 | 5.04 | 4.74 | 5.56 | 4.58 |
| ADDITIVE A | 0.20 | 0.20 | 0.20 | 0.20 | 0.20 | 0.20 | 0.20 | 0.20 | 0.20 | 0.20 | 0.20 | 0.20 |
| ADDITIVE B | 0.19 | 0.19 | 0.19 | 0.19 | 0.19 | 0.19 | 0.19 | 0.19 | 0.19 | 0.19 | 0.19 | 0.19 |
| CATALYST A (solution) | 0.98 | 0.98 | 0.98 | 0.98 | 0.98 | 0.98 | 0.98 | 0.98 | 0.98 | 0.98 | 0.98 | 0.98 |
| n-BA | 1.70 | 10.98 | 10.98 | 10.98 | 10.98 | 10.98 | 10.98 | 10.98 | 10.98 | 10.96 | 13.78 | 2.63 |
| URETDIONE A (~5) | 32.37 | | | | | | | | | | | 29.76 |
| URETDIONE B (~5) | | 22.70 | | | | | | | | | | |
| URETDIONE C (~5) | | | 22.69 | | | | | | | | | |
| URETDIONE D (~5) | | | | 22.68 | | | | | | | | |
| URETDIONE E (~5) | | | | | 22.65 | | | | | | | |
| URETDIONE F (~5) | | | | | | 22.64 | | | | | | |
| URETDIONE G (~5) | | | | | | | 22.61 | | | | | |
| URETDIONE H (~5) | | | | | | | | 22.62 | | | | |
| URETDIONE I (~5) | | | | | | | | | 22.61 | | | |
| URETDIONE J (~3.8) | | | | | | | | | | 22.94 | | 1.85 |
| URETDIONE K (~5) | | | | | | | | | | | 19.29 | |
| | | | | | Uretdione Blend | | | | | | | |
| Blend Type | — | hot | hot | hot | hot | hot | hot | hot | hot | — | — | cold |
| IPDI/HDI ratio | 100/0 | 92/8 | 83/17 | 74/26 | 65/35 | 55/45 | 45/55 | 35/65 | 24/76 | 0/100 | 0/100 | 92/8 |
| | | | | | MEK Double Rubs | | | | | | | |
| 100° C. | 140 | 350 | 343 | 340 | 195 | 127 | 124 | 87 | 79 | 48 | 52 | 106 |

| | Ex. M | Ex. N | Ex. O | Ex. P | Ex. Q | Ex. R | Ex. S | Ex. T | Ex. U | Ex. V | Ex. W | Ex. X |
|---|---|---|---|---|---|---|---|---|---|---|---|---|
| POLYOL A | 4.59 | 4.61 | 4.63 | 4.64 | 4.66 | 4.68 | 4.70 | 4.65 | 4.74 | 4.83 | 4.93 | 5.03 |
| ADDITIVE A | 0.20 | 0.20 | 0.20 | 0.20 | 0.20 | 0.20 | 0.20 | 0.20 | 0.20 | 0.20 | 0.20 | 0.20 |
| ADDITIVE B | 0.19 | 0.19 | 0.19 | 0.19 | 0.19 | 0.19 | 0.19 | 0.19 | 0.19 | 0.19 | 0.19 | 0.19 |
| CATALYST A (solution) | 0.98 | 0.98 | 0.98 | 0.98 | 0.98 | 0.98 | 0.98 | 0.98 | 0.98 | 0.98 | 0.98 | 0.98 |
| n-BA | 3.57 | 4.50 | 5.42 | 6.35 | 7.28 | 8.20 | 9.12 | 2.96 | 4.21 | 5.45 | 6.67 | 7.88 |
| URETDIONE A (~5) | 26.83 | 23.90 | 20.98 | 17.74 | 14.50 | 11.27 | 7.72 | 29.66 | 26.65 | 23.65 | 20.69 | 17.42 |
| URETDIONE B (~5) | | | | | | | | | | | | |
| URETDIONE C (~5) | | | | | | | | | | | | |
| URETDIONE D (~5) | | | | | | | | | | | | |
| URETDIONE E (~5) | | | | | | | | | | | | |
| URETDIONE F (~5) | | | | | | | | | | | | |
| URETDIONE G (~5) | | | | | | | | | | | | |
| URETDIONE H (~5) | | | | | | | | | | | | |
| URETDIONE I (~5) | | | | | | | | | | | | |

TABLE I-continued

| | | | | | | | | | | | | |
|---|---|---|---|---|---|---|---|---|---|---|---|---|
| URETDIONE J (~3.8) | 3.93 | 6.00 | 8.07 | 10.37 | 12.66 | 14.95 | 17.46 | | | | | |
| URETDIONE K (~5) | | | | | | | | 1.61 | 3.41 | 5.19 | 6.96 | 8.91 |
| | | | | | Uretdione Blend | | | | | | | |
| Blend Type | cold | cold | cold | cold | cold | cold | cold | cold | cold | cold | cold | cold |
| IPDI/HDI ratio | 83/17 | 74/26 | 65/35 | 55/45 | 45/55 | 35/65 | 24/76 | 92/8 | 83/17 | 74/26 | 65/35 | 55/45 |
| | | | | | MEK Double Rubs | | | | | | | |
| 100° C. | 111 | 76 | 75 | 76 | 76 | 52 | 62 | 13 | 114 | 93 | 77 | 80 |

| | Ex. Y | Ex. Z | Ex. AA |
|---|---|---|---|
| POLYOL A | 5.13 | 5.23 | 5.33 |
| ADDITIVE A | 0.20 | 0.20 | 0.20 |
| ADDITIVE B | 0.19 | 0.19 | 0.19 |
| CATALYST A (solution) | 0.98 | 0.98 | 0.98 |
| n-BA | 9.08 | 10.27 | 11.45 |
| URETDIONE A (~5) | 14.19 | 10.98 | 7.49 |
| URETDIONE B (~5) | | | |
| URETDIONE C (~5) | | | |
| URETDIONE D (~5) | | | |
| URETDIONE E (~5) | | | |
| URETDIONE F (~5) | | | |
| URETDIONE G (~5) | | | |
| URETDIONE H (~5) | | | |
| URETDIONE I (~5) | | | |
| URETDIONE J (~3.8) | | | |
| URETDIONE K (~5) | 10.84 | 12.75 | 14.83 |
| Uretdione Blend | | | |
| Blend Type | cold | cold | cold |
| IPDI/HDI ratio | 45/55 | 35/65 | 24/76 |
| MEK Double Rubs | | | |
| 100° C. | 62 | 58 | 57 |

As can be appreciated by reference to Table I, Examples A through AA were prepared to determine the difference between hot and cold blending of uretdione-containing resins on performance. Examples A, J, and K are reference formulations that were used for cold blending. Examples B, C, D, E, F, G, H, and I were hot blended formulations. Examples L, M, N, O, P, Q, R, S, T, U, V, W, X, Y, Z, and AA were cold blended formulations using Examples A, J, and K followed by coating formulation.

Hot and cold blended formulations were made at the same blend ratios to permit direct comparison of their performance using MEK double rubs. By comparing the MEK double rubs results, it is apparent to those skilled in the art that coatings made from formulations containing resins that were hot blended had better performance (solvent resistance) based on MEK double rubs than corresponding coatings made from formulations containing cold blended resins.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth herein. Such embodiments may be obtained, for example, by combining, modifying, or reorganizing any of the disclosed steps, components, elements, features, aspects, characteristics, limitations, and the like, of the various non-limiting embodiments described in this specification. In this manner, Applicants reserve the right to amend the claims during prosecution to add features as variously described in this specification, and such amendments comply with the requirements of 35 U.S.C. § 112(a), and 35 U.S.C. § 132(a).

Various aspects of the subject matter described herein are set out in the following numbered clauses:

1. A reaction mixture comprising a blend of a first isocyanate-based uretdione-containing resin and a second isocyanate-based uretdione-containing resin; a neutralized polyol and a tertiary amine catalyst; and optionally, an additive package selected from the group consisting of flow control additives, pigments (colorants), wetting agents, and solvents, wherein the first isocyanate and the second isocyanate are different.

2. The reaction mixture according to clause 1, wherein the tertiary amine is an amidine.

3. The reaction mixture according to clause 1, wherein the tertiary amine is selected from the group of 1,8-diazabicyclo[5.4.0]undec-7-ene, 7-methyl-1,5,7-triazabicyclo[4.4.0]dec-5-ene, 1,4,5,6-tetrahydro-1,2-dimethylpyrimidine, 1,2,4-triazole, sodium derivative and 2-tert-butyl-1,1,3,3-tetramethylguanidine, and combinations thereof.

4. The reaction mixture according to clause 1, wherein the neutralized polyol comprises the reaction product of a polyol and an acid scavenger.

5. The reaction mixture according to clause 4, wherein the acid scavenger is covalently bonded to acidic groups within the polyol and is selected from the group consisting of carbodiimides, anhydrides, epoxies, trialkylorthoformates, amine compounds, oxazolines, and combinations thereof.

6. The reaction mixture according to clause 4, wherein the polyol is selected from the group consisting of polyalkylene ether polyol, polyester polyols hydroxyl containing polycaprolactones, hydroxyl-containing (meth)acrylic polymers, polycarbonate polyols, polyurethane polyols and combinations thereof.

7. The reaction mixture according to one of clauses 1 to 6, wherein the first isocyanate and the second isocyanate are independently selected from the group consisting of 1,4-tetramethylene diisocyanate, 1,6-hexamethylene diisocyanate (HDI), 2,2,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyanatocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydrotoluene diisocyanate, toluene diisocyanate (TDI), diphenylmethane diisocyanate (MDI), pentane diisocyanate (PDI)—bio-based, and, isomers of any of these.

8. The reaction mixture according to one of clauses 1 to 7, wherein the first isocyanate-based uretdione-containing resin and the second isocyanate-based uretdione-containing resin are cold blended.

9. The reaction mixture according to one of clauses 1 to 7, wherein the first isocyanate-based uretdione-containing resin and the second isocyanate-based uretdione-containing resin are hot blended.

10. The reaction mixture according to one of clauses 1 to 9, wherein the first isocyanate is 1-isocyanato-3-isocyanatomethyl-3,5,5-trimethyl cyclohexane (isophorone diisocyanate or IPDI) and the second isocyanate is 1,6-hexamethylene diisocyanate (HDI).

11. The reaction mixture according to clause 10, wherein the ratio of 1-isocyanato-3-isocyanatomethyl-3,5,5-trimethyl cyclohexane (isophorone diisocyanate or IPDI) to 1,6-hexamethylene diisocyanate (HDI) is between 92:8 and 24:76.

12. One of a coating, an adhesive, a casting, a composite, and a sealant comprising the reaction mixture according to one of clauses 1 to 11.

13. A method of applying the reaction mixture according to one of clauses 1 to 11 to a substrate, wherein the method comprises at least one of spraying, dipping, flow coating, rolling, brushing, and pouring.

14. A method of making an allophanate polymer comprising blending a first isocyanate-based uretdione-containing resin and a second isocyanate-based uretdione-containing resin to form a resin blend, reacting the resin blend with a neutralized polyol in the presence of a tertiary amine catalyst, optionally in the presence of an additive package selected from the group consisting of flow control additives, pigments (colorants), wetting agents, and solvents, wherein the first isocyanate and the second isocyanate are different.

15. The method according to clause 14, wherein the tertiary amine is an amidine.

16. The method according to clause 14, wherein the tertiary amine is selected from the group consisting of 1,8-diazabicyclo[5.4.0]undec-7-ene, 7-methyl-1,5,7-triazabicyclo[4.4.0]dec-5-ene, 1,4,5,6-tetrahydro-1,2-dimethylpyrimidine, 1,2,4-triazole, sodium derivative and 2-tert-butyl-1,1,3,3-tetramethylguanidine, and combinations thereof.

17. The method according to one of clauses 14 to 16, wherein the neutralized polyol comprises the reaction product of a polyol and an acid scavenger.

18. The reaction mixture according to clause 17, wherein the acid scavenger is covalently bonded to acidic groups within the polyol and is selected from the group consisting of carbodiimides, anhydrides, epoxies, trialkylorthoformates, amine compounds, oxazolines, and combinations thereof.

19. The reaction mixture according to clause 17, wherein the polyol is selected from the group consisting of polyalkylene ether polyol, polyester polyols hydroxyl containing polycaprolactones, hydroxyl-containing (meth)acrylic polymers, polycarbonate polyols, polyurethane polyols and combinations thereof.

20. The method according to one of clauses 14 to 19, wherein the first isocyanate and the second isocyanate are independent selected from the group consisting of 1,4-tetramethylene diisocyanate, 1,6-hexamethylene diisocyanate (HDI), 2,2,4-trimethyl-1,6-hexamethylene diisocyanate, 1,12-dodecamethylene diisocyanate, cyclohexane-1,3- and 1,4-diisocyanate, 1-isocyanato-2-isocyanato-methyl cyclopentane, 1-isocyanato-3-isocyanatomethyl-3,5,5-trimethyl cyclohexane (isophorone diisocyanate or IPDI), bis-(4-isocyanatocyclohexyl)methane, 1,3- and 1,4-bis(isocyanatomethyl)-cyclohexane, bis-(4-isocyanato-3-methyl-cyclohexyl)-methane, α,α,α',α'-tetramethyl-1,3- and 1,4-xylene diisocyanate, 1-isocyanato-1-methyl-4(3)-isocyanato-methyl cyclohexane, and 2,4- and 2,6-hexahydrotoluene diisocyanate, toluene diisocyanate (TDI), diphenylmethane diisocyanate (MDI), pentane diisocyanate (PDI)—bio-based, and, isomers of any of these.

21. The method according to one of clauses 14 to 20, wherein the first isocyanate-based uretdione-containing resin and the second isocyanate-based uretdione-containing resin are cold blended.

22. The method according to one of clauses 14 to 20, wherein the first isocyanate-based uretdione-containing resin and the second isocyanate-based uretdione-containing resin are hot blended.

23. The method according to one of clauses 14 to 22, wherein the first isocyanate is 1-isocyanato-3-isocyanatomethyl-3,5,5-trimethyl cyclohexane (isophorone diisocyanate or IPDI) and the second isocyanate is 1,6-hexamethylene diisocyanate (HDI).

24. The method according to clause 23, wherein the ratio of 1-isocyanato-3-isocyanatomethyl-3,5,5-trimethyl cyclohexane (isophorone diisocyanate or IPDI) to 1,6-hexamethylene diisocyanate (HDI) is between 92:8 and 24:76.

25. An allophanate polymer made according to the method of one of clauses 14 to 24.

26. One of a coating, an adhesive, a casting, a composite, and a sealant comprising the allophanate polymer made according to one of clauses 14 to 24.

27. A method of applying the allophanate polymer made according to one of clauses 14 to 24 to a substrate, wherein the method comprises at least one of spraying, dipping, flow coating, rolling, brushing, and pouring.

What is claimed is:

1. A reaction mixture comprising:
   a hot blend of a 1-isocyanato-3-isocyanatomethyl-3,5,5-trimethyl cyclohexane (isophorone diisocyanate or IPDI)-based uretdione-containing resin and a 1,6-hexamethylene diisocyanate (HDI)-based uretdione-containing resin, wherein the hot blend is at an IPDI-uretdione/HDI-uretdione weight ratio of from 92/8 to 45/55;
   a neutralized polyester polyol comprising the reaction product of a polyester polyol and an acid scavenger; and
   a tertiary amine catalyst comprising 1,8-diazabicyclo[5.4.0]undec-7-ene, and
   optionally, a hydrocarbon solvent,
   optionally, an additive package selected from the group consisting of flow control additives, pigments, wetting agents, and solvents.

2. The reaction mixture according to claim 1, wherein the acid scavenger is covalently bonded to acidic groups within the polyester polyol and is selected from the group consisting of carbodiimides, anhydrides, epoxies, trialkylorthoformates, amine compounds, oxazolines, and combinations thereof.

3. One of a coating, an adhesive, a casting, a composite, and a sealant comprising the reaction mixture according to claim 1.

4. A method of applying the reaction mixture according to claim 1 to a substrate, wherein the method comprises at least one of spraying, dipping, flow coating, rolling, brushing, and pouring.

5. A method of making an allophanate polymer comprising:
hot blending a 1-isocyanato-3-isocyanatomethyl-3,5,5-trimethyl cyclohexane (isophorone diisocyanate or IPDI)-based uretdione-containing resin and a 1,6-hexamethylene diisocyanate (HDI)-based uretdione-containing resin to form a resin blend, wherein the hot blending is at an IPDI-uretdione/HDI-uretdione weight ratio of from 92/8 to 45/55;
reacting the resin blend with a neutralized polyester polyol in the presence of a tertiary amine catalyst and optionally a hydrocarbon solvent, optionally in the presence of an additive package selected from the group consisting of flow control additives, pigments, wetting agents, and solvents,
wherein the neutralized polyester polyol is the reaction product of a polyester polyol and an acid scavenger and wherein the tertiary amine catalyst is 1,8-diazabicyclo[5.4.0]undec-7-ene.

6. The method according to claim 5, wherein the acid scavenger is covalently bonded to acidic groups within the polyester polyol and is selected from the group consisting of carbodiimides, anhydrides, epoxies, trialkylorthoformates, amine compounds, oxazolines, and combinations thereof.

7. An allophanate polymer made according to the method of claim 5.

8. One of a coating, an adhesive, a casting, a composite, and a sealant comprising the allophanate polymer made according to claim 5.

9. A method of applying the allophanate polymer made according to claim 5 to a substrate, wherein the method comprises at least one of spraying, dipping, flow coating, rolling, brushing, and pouring.

* * * * *